United States Patent [19]

Webb

[11] Patent Number: 5,422,376

[45] Date of Patent: Jun. 6, 1995

[54] SYNTHETIC VISCOELASTIC MATERIAL FOR OPHTHALMIC APPLICATIONS

[76] Inventor: Bradford C. Webb, 1309 Danielson Rd., Santa Barbara, Calif. 93108

[21] Appl. No.: 240,941

[22] Filed: May 11, 1994

Related U.S. Application Data

[63] Continuation of Ser. No. 55,822, Apr. 30, 1993, abandoned.

[51] Int. Cl.$^6$ .............................................. A61K 47/00
[52] U.S. Cl. .................................... 514/781; 514/912
[58] Field of Search ............................... 514/781, 912

[56] References Cited

U.S. PATENT DOCUMENTS

| | | |
|---|---|---|
| 4,343,787 | 8/1982 | Katz . |
| 4,819,617 | 4/1989 | Goldberg et al. . |
| 4,853,374 | 8/1989 | Allen . |
| 5,013,714 | 5/1991 | Lindstrom et al. . |
| 5,218,107 | 6/1993 | Schulz ................................. 536/84 |

FOREIGN PATENT DOCUMENTS

| | | |
|---|---|---|
| 62-122671 | 6/1987 | Japan . |
| 62-266056 | 11/1987 | Japan . |
| 2204238 | 11/1988 | United Kingdom . |

OTHER PUBLICATIONS

Arshinoff, Steve, "Comparative Physical Properties of Ophthalmic Viscoelastic Materials", *Ophthalmic Practice*, vol. 7, No. 1 (1989).
Arshinoff, Steve, "The Physical Properties of Ophthalmic Viscoelastics in Cataract Surgery", *National Ophthalmic Speakers Program*, pp. 7–12 (1992).
Arshinoff, Steve, "The Safety and Performance of Ophthalmic Viscoelastics in Cataract Surgery and Its Complications", *National Ophthalmic Speakers Program*, pp. 21–28 (1994).
Bothner, H., et al., "Rheology of Intraocular Solutions", *Viscoelastic Materials, Vision and Visual Health Care*, vol. 2 (1986), pp. 53–70.
Rosen E., et al., "Some Observations On Hydroxypropylmethylcellulose", *Viscoelastic Materials, Vision and Visual Health Care*, vol. 2 (1986), pp. 1–7.
McG Steele, A. D. "Hydroxypropylmethylcellulose Used As A Viscoelastic Fluid In Ocular Surgery", *Viscoelastic Materials, Vision and Visual Health Care*, vol. 2 (1986), pp. 27–29.
Dow Chemical, "How to Improve Pharmaceutical Formulations with METHOCEL and ETHOCEL Cellulose Ethers," Oct. 1995.
Dow Chemical, "Formulating for Controlled Release with METHOCEL cellulose ethers," pp. 1–9, Mar. 1987.
Dow Chemical, "METHOCEL Cellulose Ethers Technical Handbook," pp. 1–24, Apr. 1988.
Robert, Y., Gloor, B., Wachsmuth, E. D., Herbst, M., "Die Uberprufung der Vertraglichkeit von Intraokular injizerter Hydroxypropylmethylcellulose im Tierversuch," *Klin Monatsbl Augenheilkd*, 192:337–339, 1988.
Rosen, E. S., Gregory, R. P. F., Barnett, F., "Is 2% hydroxypropyl methylcellulose a safe solution for intraoperative clinical applications?" *J. Cataract and Refractive Surgery*, 12:679 (1986).
Rosen, E. S., "The use of hydroxypropyl methylcellu- (List continued on next page.)

*Primary Examiner*—Zohreh Fay

[57] ABSTRACT

A viscoelastic composition for injection into a human eye comprised of about 2.0 to 2.5 percent of hydroxypropyl methylcellulose dissolved in a physiological salt solution, the composition, the composition having a viscosity from about 15,000 to about 40,000 centipoise and the hydroxypropyl methylcellulose having a molecular weight from about 220,000 to less than about 420,000 Daltons, the composition being free of debris or gels greater than 0.5 μm. Also described is a process for preparing the clean, high molecular weight hydroxy propylmethyl cellulose composition.

26 Claims, No Drawings

OTHER PUBLICATIONS lose in extracapsular cataract extraction with intraocular lens implantation," *Am J. Ophthalmology,* 103:727-728 (1987).

Momose, A., Baba, T., Kasahara, A., "Particles in Viscosurgical Materials," *Journal of the Eye,* 5:314 (1988).

Fernandez-Vigo, J. F., Refojo, M. F., Jumblatt, M., "Elimination of hydroxypropylmethylcellulose from the anterior chamber of the rabbit," *J. Cataract Refractive Surgery,* 15:191 (1989).

"Methylcellulose," *IOL* 1: 147-151, 1987.

Jacobi, K. W., Schott, K., Gloor, B., "Kongress der Deutschen Gesellschaft fur Intraokularlinsen Implantation," *Berlin, Springer-Verlag,* 1987 pp. 86-89.

Fechner, P. U., Rimpler, M., "Comparison of Hydroxypropyl methylcellulose 2% (Adatocel) and hyaluronic acid 1% (Healon)", *J. Cataract Refract. Surg.,* vol. 11, Nov. 1985.

Fechner, P. U., "Preparation of 2% Hydroxypropyl Methylcellulose for Viscous Surgery", *Am. Interocular Implant Soc. J,* vol. 11, No. 1985.

Hazariwala, K, Mortimer, C. B., Slomovic, "Comparison of 2% Hyrdroxypropyl Methylcellulose and 1% Sodium Hyaluronate in Implant Surgery", *Can. J. Opthtal.* 23(6), 1988, pp. 259-261.

Bigar, F., Gloor, B., Schimmelpfennig, B. Thumm, D. "The tolerance of Hydopropylmethylcellulose in Implantation of Posterior Chamber Lenses", *Klin. Monatsbl. Augenheilkd,* 193(1), 1988, pp. 21-24.

Dow Chemical Sales Specification—Methocell E10M, Jun. 9, 1992, (three pages).

Dow Chemical Sales Specification—Methocel K100M, Sep. 4, 1991 (three pages).

SYNTHETIC VISCOELASTIC MATERIAL FOR OPHTHALMIC APPLICATIONS

This is a continuation of application Ser. No. 08/055,822, filed Apr. 30, 1993 now abandoned.

BACKGROUND

The present invention relates to a viscoelastic material for use in medical procedures, particularly for placement into the eye during ophthalmic surgical procedures to maintain the shape of the eye and to protect delicate tissue lining the inner walls of the eye.

Cataracts in human eyes, a clouding of the lens which severely effects vision and can render an individual blind, have been removed by surgical procedures for centuries. One of the earliest techniques, known as couching, utilized a long thorn to pry lose the clouded lens. However, safe and effective cataract removal followed by the implantation of an artificial lens has been practiced only since the early 1970's. Prior to then the patient was usually fitted with thick glasses in an attempt to provide at least some acceptable level of vision after removal of the clouded lens. Cataract removal and artificial lens implantation is now performed in the United States on over one million patients per year.

One of the hazards of the cataract removal and lens implantation procedure is the fact that the inside cell layer of the cornea (corneal endothelium) as well as other internal tissues is very sensitive to abrasion or inadvertent contact. In particular, damage to, or removal of, the cells on the cornea may compromise corneal physiology and lead to corneal edema, opacification and eventually complete loss of the cornea.

As a result, a great deal of effort has been devoted to protecting the corneal endothelium, during cataract surgery. In particular, various different materials have been injected into the anterior portion of the eye including balanced salt solution, an air bolus (both of limited utility as they are easily dispersed from the eye) and viscoelastic materials. Viscoelastic materials prepared from various naturally occurring substances or synthesized in the laboratory include sodium hyaluronate, chondroitin sulfate and combinations thereof, cellulosic materials, and polymers based on acrylamide. While viscoelastic materials remain in the eye and offer better protection to the ocular tissue, each of the prior used viscoelastics have disadvantages which included allergic reactions, neurotoxic impurities, inadequate viscosity or viscoelasticity, unacceptable levels of particulate materials, gels or bulky polymer chains which enter and plug the trabecular mesh work causing excessive intraocular pressure in the eye, variation in properties from batch to batch due to variability of naturally occurring raw materials, and excessive cost. These materials, because they result in increased ocular pressure also generally require that they be irrigated from the eye. Further, hyaluronic acid based materials also require refrigerated storage and may have a limited shelf life.

The use of prior art hydroxypropylmethylcellulose solutions in animal toxicity studies has shown that these materials are generally non-toxic both locally and systemically when ingested or injected into various animal systems. Also, various prior art HPMC formulations in intraocular use have been shown to be non-toxic to endothelial cells and to result in only minimal and transient intraocular pressure rise and to clear the eye rapidly.

Dow Chemical Company has studied the toxicology and metabolic fate of HPMC polymers extensively to support the use of their Methocel trademark HPMC. These studies have shown that the polymer is non-pyrogenic, non-immunogenic, non-cytotoxic, non-toxic in extended animal metabolic studies, is not metabolized and is rapidly eliminated after ingestion. The majority of these reports deal with the tolerance of animal systems to HPMC via feeding studies. However, a review of the data on toxicology reveals that intradermal and vascular injections of HPMC polymers in mice and rats do not provide any evidence of toxicity, teratogenicity, or other negative metabolic effects. It is concluded from these reports that HPMC polymers do not interfere with normal animal metabolism, are not themselves metabolized, and are filtered from the bloodstream into the kidneys and excreted without negative effects to the animal systems studied. In confirmation of these studies, the Dow Chemical Company Methocel brand of HPMC has been issued Drug Master File No. 76 by the Food and Drug Administration.

Robert et al have provided evidence of the lack of systemic toxicity of intraocular injections of 2% HPMC solutions into rabbit eyes. (Robert, Y., Gloor, B., Wachsmuth, E. D., Herbst, M., "Die Uberprufung der Vertraglichkeit von Intraokular injizerter Hydroxypropylmethylcellulose im Tierversuch," *Klin Montasbl Augenheilkd*, 192:337–339, 1988.) These researchers injected aliquots of a 2% HPMC solution into rabbit anterior chambers, and into rabbit posterior chamber vitreous, and followed the course of intraocular and systemic changes for 12 days. They found no intraocular changes, and also no systemic changes. These results clearly demonstrate that the HPMC polymer is non-toxic to the animal eyes and is systemically non-toxic in rabbits.

The available evidence in the literature demonstrates that HPMC is not metabolized by mammalian systems, is non-toxic on oral, intradermal, intraocular and vascular introduction, and is safely cleared from the systems via excretion in the urine. Thus it may be inferred from these reports that HPMC solutions are safe for human intraocular and systemic use.

HPMC solutions have been used as intraocular viscoelastic surgical fluids for several years in Europe, the USA, and elsewhere. The literature reports on the clinical use of HPMC solutions reflect a general consensus that these polymers are safe and effective for use as ophthalmic viscoelastic surgical fluids, easy to use and do not result in inflammatory reactions or excessive intraocular pressure postoperatively, but are only marginally equivalent to hyaluronic acid products in ability to maintain the chamber and protect the endothelium during cataract surgery.

However, the use of HPMC solutions for intraocular surgery has been criticized by Rosen. (Rosen, E. S., Gregory, R. P. F., Barnett, F., "Is 2% hydroxypropyl methylcellulose a safe solution for intraoperative clinical applications?" *J. Cataract and Refractive Surgery*, 12:679 (1986); Rosen, E. S., "The use of hydroxypropyl methylcellulose in extracapsular cataract extraction with intraocular lens implantation," *Am J. Ophthalmology*, 103:727 (1987)). Rosen bases his criticism on the microscopic examination of HPMC preparations produced by hospital pharmacies in Europe. Rosen reports that significant amounts of debris and particulates are found in these and other commercial preparations, which could lead to problems during surgical use. Further, Rosen states that current attempts to filter HPMC have been ineffective and "it seems to be impossible to prepare HPMC solutions for clinical use without a degree of particulate vegetable matter content." However, Momose et al report that counts of the particulate levels by automated laser particle counters reveal that 2% methylcellulose preparations prepared in his institute actually had fewer large particles than commercially available hyaluronic acid preparations. (Momose, A., Baba, T., Kasahara, A., "Particles in Viscosurgical Materials," *Journal of the Eye,* 5:314 (1988)).

Fernandez-Vigo et al. reported in 1989 that the half life of clearance of various concentrations and viscosities of HPMC solutions from rabbit eyes was in the range of 3 to 4 ½ hr. (Fernandez-Vigo, J. F., Refojo, M. F., Jumblatt, M., "Elimination of hydroxypropylmethylcellulose from the anterior chamber of the rabbit," *J. Cataract Refractive Surgery,* 15:191 (1989)). Their experiments involved introduction of large doses of relatively low molecular weight HPMC solutions (86,000 or 120,000 Daltons) into rabbit eyes, and assays of the HPMC remaining after various periods of time. They found that after 24 hr., there were no detectable amounts of HPMC remaining in the samples of aqueous removed from the rabbit eyes. They concluded that HPMC clearance was complete within 24 hrs. The authors also concluded that the removal of the HPMC from the eye was by the normal trabecular meshwork outflow system, with no metabolic degradation within the eye. Their report further found no damage to endothelial cells, only a transient increase in intraocular pressure after the injection of the HPMC solutions within the eye, and no long term inflammatory reactions.

Jacobi et al reported that their studies of the intraocular (anterior chamber and intravitreal) injections of HPMC solutions into the rabbit resulted in no inflammatory reactions, only transient rise in intraocular pressure, and rapid clearance from the eye. (Jacobi, K. W., Schott, K., Gloor, B., "Kongress der Deutschen Gesellschaft fur Intraokularlinsen Implantation," *Berlin, Springer-Verlag,* 1987 pp 86–89.) They concluded that the HPMC was cleared from the eye by the normal outflow mechanism, and was diluted into the bloodstream.

These published evaluations of the rapid clearance of HPMC polymer from the eye demonstrate that this polymer does not interfere biochemically with the normal aqueous clearance through the trabecular meshwork, and only raises intraocular pressure transiently due solely to its high molecular weight and viscosity.

However, these solutions still contain unnecessarily high levels of particulate contamination. Additionally, the prior art solutions are composed of low molecular weight HPMC materials and thus, to obtain the desired viscosity higher concentrations of HPMC must be used, thus increasing the possibility of introducing a higher percentage of contaminants. Further, because the polymers have a lower molecular weight, the solutions may not have a suitable viscoelasticity. The prior art ophthalmic HPMC solutions, because they were prepared from lower molecular weight materials had viscosities of about 4,000 to 5,000 cps at 25° C. As a result, these materials also were not very viscoelastic. Additionally, they had high levels of particulate material. As a result, they could not be filtered through a 0.5 µm filter as the filter pores became immediately plugged as the material passed through the filter. A further problem with prior art HPMC solutions was the tendency to dehydrate when autoclaved at temperatures above 100° C. resulting in large amorphous aggregates. Most of these aggregates would rehydrate upon cooling but a significant portion remained permanently insoluble. Prior art autoclaving and cooling procedures following autoclaving also resulted in the release and suspension of gas bubbles in the resultant gels and the compositions did not have a uniform viscosity distribution, the more viscous, higher molecular weight materials tending to settle to the lowest point in the container.

Thus there is a need for a low cost, stable, high viscosity material for use in ocular surgical procedures which is nontoxic and allergy free and is free of particulate material or gels which can cause an increase in intraocular pressure. In particular, there is a need for a high viscosity, low HPMC concentration solution prepared from high molecular weight material which is substantially free of harmful particulate material.

SUMMARY

These needs are met by the present invention which comprises a viscoelastic material composed of hydroxypropyl-methylcellulose in an aqueous physiological solution and a process for preparing the solution. The solution also contains salts of sodium, potassium, calcium and magnesium whose concentrations are chosen so that the formulation has an osmolality slightly greater than human aqueous, a calcium concentration almost identical to that of human aqueous, and a pH approaching physiological. Additionally, the composition is purified to remove inflammatory materials and processed to tailor the weight average molecular weight to greater than 375,000 but less than 420,000 and a static viscosity of 25,000 to 40,000 centipoise at 25° C. as measured by a capillary viscometer.

These and other features, aspects and advantages of the present invention will become better understood with reference to the following description and appended claims.

DESCRIPTION

The present invention consists of a viscous, aqueous solution of a hydroxypropylmethylcellulose (HPMC) for use in ocular applications and the method for preparation of these unique solutions. Other components of the solutions embodying features of the invention can be NaCl, KCl, $CaCl_2$, MgCl and Na based buffers such as $NaC_2H_3O_2$ or $Na_3C_6HO_7$. The concentrations of the components of the HPMC solutions were derived to have an osmolality and pH based on the aqueous solution in the human eye. The osmolality of human aqueous is about 305 mOsm/kg ($\pm 25$ mOsm/kg). Accordingly, the NaCl concentration in the viscous solution was adjusted to be about 325 mOsm/kg ($\pm 25$ mOsm/kg) to minimize swelling of the corneal endothelial cells during use in the eye. The pH of human aqueous is about 7.4; the pH of the HPMC solution was adjusted to a final pH of about 7.2$\pm$0.2. The concentration of the other salts and the buffering agents were chosen to be similar to that of commercially available intraocular irrigating solutions and viscoelastic surgical fluids.

In formulating the solutions of the invention, one of the concerns was the formation of precipitates during use as was reported for a commercially available chondroitin sulfate/sodium hyaluronate solution. (Ullman, S., Lichtenstein, S. B., Heerlein, K., "Corneal Opacities Secondary to Viscoat," *J. Cataract and Refractive Surgery*, 12:489 (1986)). This was accomplished by keeping the calcium concentration to approximately the same level as in human aqueous and avoiding the use of phosphates in the buffering components. This eliminates the possibility of the formation of $Ca_3(PO_4)_2$. Tests in rabbit eyes have confirmed the absence of precipitates.

Of particular concern in the preparation of solutions embodying features of the invention was the possibility of inflammatory responses caused by trace impurities in the materials or the presence of particulate contaminates, particularly in the HPMC, which is critical to the invention. Accordingly, extensive steps have been taken to eliminate the undesirable trace contaminates. Additionally, multiple filtration and separation procedures have been utilized to generate HPMC materials having a narrow preferred molecular weight and to eliminate changes in this preferred molecular weight which can result from high temperature sterilization of the solution.

Prior HPMC solutions had viscosities from 4,000 to 5,000 cps at 25° C. In contrast thereto, viscosities in the range of 15,000 to 40,000 cps can be obtained by using a blend of a high and a low molecular weight HPMC material. The higher molecular weight material results in the much improved viscoelasticity. A preferred blend consists of a 2:1 ratio of a 85,000 average molecular weight material with a 220,000 average molecular weight material, the initial composition having about 3% HPMC. Processing as described below significantly reduces the concentration of the low molecular weight materials so that the average molecular weight of the remaining material ranges from 250,000 to about 420,000. However, the preferred range of the average molecular weight of the HPMC remaining in the solution is from about 375,000 to no greater than about 420,000 Daltons and the preferred solution viscosity is from about 25,000 to about 40,000 centipoise.

A preferred starting material for preparing the high viscosity, toxicity and particulate free solutions of the invention are HPMC polymers available from Dow Chemical Company under the tradename Methocel ©. In contrast to the prior art HPMC solutions, a particular preferred starting materials is a blend of a low molecular weight HPMC (Methocel E10M) and a high molecular weight HPMC material (Methocel K100M) the two materials being initially blended in the ratio of 2:1. The two materials are reported to have the following viscosities:

Methocel E10M: 2% viscosity=14,000 cps
Methocel K100M: 2% viscosity=100,900 cps

While the initial combined concentration of the HPMC materials is about 3.0%, after the filtration procedures are completed the concentration of the HPMC materials in the solution is reduced to about 2.0 to 2.5%.

Processing steps which result in the unique properties of the solutions embodying features of the invention are as follows:

Removal of Particulate Contamination—The previous technique used to filter HPMC solutions was to force the solution through a 0.5 $\mu$m filter at a high pressure. However, since a significant portion of the material to be removed was gelatinous in nature the pressure merely reshaped the gels and forced them through the pores of the filter. In addition, at very high pressure, the filter would plug up and only salt solution would be forced through the filter. It was discovered that greatly improved filtration could be obtained by raising the temperature of the solution to about 40°–45° C. resulting in a significant reduction in viscosity, thus requiring less pressure. Secondly, the solution was passed through a series of successively smaller filters so that the larger gels and particles could be removed before they reached the smallest filters. A suitable filtration procedure included passing the solution at least twice through a cascade consisting of a 50 $\mu$m, 25 $\mu$m, 10 $\mu$m, 5 $\mu$m, 1 $\mu$m and a 0.5 $\mu$m filters. This procedure eliminates the need for excessive pressure during filtration and virtual eliminates all material above 0.5 $\mu$m in size.

Processing described below significantly reduces the concentration of the low molecular weight materials.

Purification—In order to remove all undesirable low molecular weight material the dry HPMC blend is suspended with constant stirring in a salt solution at 60° C., which is lower than the literature recommended temperature of 100° C. for forming solutions. This allows the polymer granule pore structure of the HPMC to expand and the lower molecular weight materials to solvate. When the HPMC is solvated at the higher temperature the low molecular weight material becomes trapped in the resultant gel and can't be readily separated. Once the low molecular weight material has been solvated the composition can be raised slowly with constant stirring to around 100° C. Stirring is then terminated and the high molecular weight material is allowed to settle to the bottom of the mixing chamber. Once the settling has ceased the supernatant liquid containing the undesirable low molecular weight material is carefully removed and discarded. The process is repeated several times, four times appearing to be optimal. This procedure removes the low molecular weight contaminates and pyrogens which, in turn, results in a higher viscosity final solution.

Removal of Aggregates Caused by Autoclaving—An intermediate (midprocess) autoclaving and filtering step is performed to eliminate aggregates which don't readily rehydrate. The procedure consisting of heating the composition to 115° C., in an autoclave cooling with rapid stirring to 95° C. to break up aggregates and assure homogeneous rehydration, further cooling to 40° C., and filtering through a 1.0 $\mu$m filter to remove undissolved HPMC aggregates. This eliminates the possibility of aggregates forming during the final autoclaving step. This step also eliminates any bioburden so that solution storage problems caused by bacterial contamination don't arise.

Elimination of Non-homogeneous Viscosity Regions—If the product is cooled too rapidly after final autoclaving in the syringe, the more viscous material tends to settle to the bottom of the delivery syringe resulting in a layering of the composition. In contrast, if the solution filled syringe is allowed to cool slowly from 90° C. to room temperature at a rate of less than about 6° C. per hour a very uniform gel is formed.

Elimination of Bubble Formation—Dissolved gases released during processing become entrapped in the viscous solution. If they are not removed prior to the final product packaging stage the final product will include gas bubbles which can obscure the physicians visualization of the surgical site during the ophthalmic procedure.

EXAMPLE 1

FIG. 1 is a flow chart showing the process of Example 1 which embodies features of the present invention.

a) 30 liters of a salt solution was prepared by adding 174 grams of NaCl, 22.5 grams of KCl, 14.4 grams of $CaCl_2.2H_2O$, 9.0 grams of $MgCl.6H_2O$, 117.0 grams of $NaC_2H_3O_2.3H_2O$ and 51.0 grams of $Na_3C_6HO_7.2H_2O$ to distilled water and the pH was adjusted to 8.70 using NaOH.

b) Five (5) liters of the salt solution were then heated to 60° C. and a mixture of 300 gr of Methocel E10M and 150 gr of Methocel K100M were stirred into the salt solution and held at temperature for 20 minutes. The composition was then heated with stirring to 95° C. and held at temperature for 20 minutes. Stirring was then discontinued and the solution allowed to settle for about 15 minutes at which point the supernatant liquid was aspirated off.

c) The polymer remaining after removal of the supernatant was then resuspended in 4.0 liters of the salt solution at 100° C. and stirred for ten minutes. The solution was then allowed to settle for 15 minutes followed by aspiration of the supernatant. The procedure was then repeated two more times using 3.0 liters of salt solution for resuspension.

d) After removing the supernatant following the third resuspension the remaining polymer was again resuspended in 15 liters of the salt solution at 100° C. and stirred for 5 hours while cooling slowly to 40° C. The solution was then held without stirring for 5 hours, allowing a thick gel to form.

e) While maintaining 40° C., the gel was filtered through a series of filters having a porosity of 50 μm, 25 μm, 10 μm, 5 μm, 1 μm and 0.5 μm. At least two of each filter size were used.

f) The material that passed through the final filter was heated to 115° C. in a pressure autoclave (12 psi.) for 25 minutes, cooled slowly for about 30 minutes to 99° C., removed from the autoclave and cooled over a five hour period to 40° C. and then held for 5 hours at 40° C. while being maintained under sterile conditions.

g) While maintaining sterility, the solution was passed through a 1.0 μm filter, collected in a 10 liter vessel and, while being maintained at 40° C., subjected to a vacuum for 10 hours to outgas any dissolved nitrogen. The degassed, sterile solution was then dispensed aseptically into storage containers which were stored at 0° to 4° C.

h) The process was completed by aseptically dispensing the stored solution into syringes which were autoclaved at 121° C. for 20 minutes, cooled to room temperature at 6° C. per hour, and then pressurized for 24 hours at 20 psi.

The resultant product was a clear, viscous solution having a zero shear viscosity of 40,000 cps, an average molecular weight of 409,800, an HPMC concentration of 2.32% and a refractive index of 1.333.

The solution prepared in Example 1 was tested both biologically and in animals. A single maximum dose evaluation was conducted in the rabbit eye model, with evaluation of intraocular pressure, endothelial cell status, and general inflammatory response. The rabbit eye model is commonly used for evaluation of endothelia cell, intraocular pressure, and inflammatory response to viscoelastics as well as acute endothelial cell toxicity studies. Other tests were performed to evaluate systemic antigenicity, cytotoxicity, and irritability in animal models, and mutagenicity and hemolytic activity in in vitro models. The results are summarized below:

| Test | Result |
| --- | --- |
| Cytotoxicity, Agarose Overlay | Non-cytotoxic |
| Cytotoxicity, MEM Elution | Non-cytotoxic |
| Intraocular Irritation in the Rabbit with tonometry and specular photography | Non-irritant and non-toxic |
| Mutagenicity, Ames Soluble Chemical | Non-mutagenic |
| Sensitization (Maximization Method), in Guinea Pig | Non-sensitizing |
| Hemolysis, In vitro Direct Contact | Non-hemolytic |
| Systemic Antigenicity in Guinea Pig | Non-antigenic |
| Primary Skin Irritation Rabbit | Non-irritant |
| Acute Oral Toxicity | Non-toxic |
| Acute Intraperitoneal Toxicity in Mouse | Non-toxic |

It was concluded from these studies that the HPMC solution is non-toxic, non-mutagenic, non-antigenic, non-hemolytic, non-irritating, non-inflammatory to ocular tissues, and did not cause a dangerous intraocular pressure rise. Further, the material had no effect on the ability of the cells to undergo normal mitotic division and, subsequently, normal cellular growth. Intraocular pressure increases in the rabbit from a maximum dose were transient and, in all cases, were within the normal range within a 24 hour period. Endothelial cells were not affected.

Although the present invention has been described in considerable detail with reference to a certain preferred versions and uses thereof, other versions and uses are possible. For example, while the viscoelastic solution is designed for ophthalmic applications, it may be used for other physiological applications such as lubricating bone joints (knees, hips, etc.), preventing tissue adhesion following surgical procedures, or as a carrier for nutritional products or cosmetics. Also, the viscosity of the solutions can be varied by selecting different molecular weight starting materials or blending the materials in different proportions or using higher concentrations of the starting materials. While a particular blend of HPMC materials is disclosed the combination selected and concentrations can depend on the desired properties of the end product. Therefore, various different HPMC may be used. Further, it is not necessary that two different materials be used. One HPMC material may be processed as described above or a blend of more than two materials may be used. Additionally, different salts and buffers can be used for different applications and other materials can be added to the solutions for special purposes. Further, one skilled in the art will recognize that a different combination of filters may be used to remove debris and, depending on the dimensions and nature of debris in the composition, one or more of each size of filter can be used. Also, the order in which various processing steps are performed may be interchanged. Therefore, the spirit and scope of the appended claims should not be limited to the description of the preferred versions contained herein.

What is claimed is:

1. An improved composition for physiological applications, said composition containing hydroxypropylmethylcellulose in a physiological salt solution, the improvement comprising a hydroxypropylmethylcellulose solution free of particulate matter and gels greater than 0.5 μm in diameter, said viscoelastic solution having a zero shear viscosity in excess of 15,000 cps, an average molecular weight in excess of 250,000 Daltons and being pyrogen free and non-toxic when a therapeutically effective amount of said solution is injected into a human body.

2. The improved composition of claim 1 wherein said composition being pyrogen free and non-toxic when a therapeutically effective amount of the solution is injected into a human eye.

3. The viscoelastic solution of claim 2 wherein the hydroxypropylmethylcellulose is present in a concentration from about 2.0% to about 2.5%.

4. The viscoelastic solution of claim 2 wherein the viscosity of the solution is from about 25,000 centipoise to about 40,000 centipoise.

5. The viscoelastic solution of claim 2 wherein the average molecular weight of the hydroxypropylmethylcellulose is greater than about 375,000 but less than 420,000.

6. The viscoelastic solution of claim 2 prepared from a blend of a first hydroxypropylmethylcellulose having a first molecular weight and a second hydroxypropylmethylcellulose having a greater molecular weight, the blend being processed to produce the particulate free, pyrogen free, and non-toxic solution.

7. The viscoelastic solution of claim 6 wherein the blend is processed by filtration, redissolving and removal of low molecular weight material, mid-process autoclaving and removal of dissolved gases.

8. The viscoelastic solution of claim 7 wherein the hydroxypropylmethylcellulose in the viscoelastic solution after processing has an average molecular weight greater than the average molecular weight of the first hydroxypropylmethylcellulose or the second hydroxypropylmethylcellulose.

9. The viscoelastic solution of claim 6 wherein the first hydroxypropylmethylcellulose has an average molecular weight of about 85,000 and the second hydroxypropylmethylcellulose has an average molecular weight of about 220,000.

10. The viscoelastic solution of claim 8 wherein the average molecular weight of the hydroxypropylmethylcellulose after processing is greater than 375,000 but less than 420,000.

11. The viscoelastic solution of claim 6 having a hydroxypropylmethylcellulose concentration of about 2.3%.

12. The viscoelastic solution of claim 5 wherein the hydroxypropylmethylcellulose has an average molecular weight of about 410,000.

13. A process for preparing a viscoelastic solution of hydroxypropylmethylcellulose in a physiological salt solution, the composition being free of particulate material and gels greater than 0.5 μm in diameter and being pyrogen free and non-toxic when a therapeutically effective amount of said solution is injected into a human eye, the process comprising the steps of:

a) dispersing the hydroxypropylmethylcellulose in the salt solution to form a suspension, b) heating the suspension of step (a) to about 95° C., allowing any undissolved material to settle and discarding the supernatant liquid above the undissolved material, c) resuspending the undissolved material to form a second suspension of hydroxypropylmethylcellulose and heating the second suspension to form a thick gel, d) filtering the gel through a series of filters, the series including a final filter having 0.5μm openings to form a clean solution, e) autoclaving the clean solution, f) cooling the autoclaved clean solution and filtering the cooled solution, and g) degassing the filtered cooled solution.

14. The process of claim 13 wherein the physiological salt solution has a pH of about 8.7 and contains NaCl, KCl, $CaCl_2.2H_2O$, $MgCl.6H_2O$, $NaC_2H_3O_2.3H_2O$, $Na_3C_6HO_7.2H_2O$.

15. The process of claim 13 wherein the hydroxypropylmethylcellulose dispersed in the aqueous salt solution is a blend of a first hydroxypropylmethylcellulose having a first molecular weight and a second hydroxypropylmethylcellulose having a higher molecular weight.

16. The process of claim 15 wherein the first hydroxypropylmethylcellulose has a molecular weight of about 85,000 Daltons and the second hydroxypropylmethylcellulose has a molecular weight of about 220,000 Daltons.

17. The process of claim 15 wherein the weight of the first hydroxypropylmethylcellulose in the suspension is about the weight of the second hydroxypropylmethylcellulose.

18. The process of claim 15 wherein the hydroxypropylmethylcellulose in the suspension is about 3% by weight.

19. The process of claim 13 wherein the concentration of the hydroxypropylmethylcellulose in the degassed solution is from about 2.0% to about 2.5%.

20. The process of claim 13 wherein the concentration of the hydroxypropylmethylcellulose in the degassed solution is about 2.3%.

21. The process of claim 13 wherein the viscosity of the degassed solution is from about 25,000 centipoise to about 40,000 centipoise.

22. The process of claim 13 wherein the viscosity of the degassed solution is about 40,000 centipoise.

23. The process of claim 13 wherein the molecular weight of the hydroxypropylmethylcellulose in the degassed solution is greater than about 375,000 but less than about 420,000.

24. The process of claim 11 wherein the molecular weight of the hydroxypropylmethylcellulose in the degassed solution is about 410,000.

25. A viscoelastic composition for injection into a human eye, the viscoelastic composition comprising hydroxypropylmethylcellulose in a physiological salt solution, the hydroxypropylmethylcellulose having an average molecular weight greater than about 375,000 but less than about 420,000 and being present in a concentration from about 2.0% to about 2.5%, the composition having a viscosity from about 25,000 centipoise to about 40,000 centipoise, being free of particulate matter and gels greater than 0.5 μm in diameter and being pyrogen free and nontoxic.

26. The viscoelastic composition of claim 25 wherein the concentration of the hydroxypropylmethylcellulose is about 2.3%, the average molecular weight of the hydroxypropylmethylcellulose is about 409,800 and the zero shear viscosity of the composition is about 40,000 centipoise.

* * * * *

UNITED STATES PATENT AND TRADEMARK OFFICE
CERTIFICATE OF CORRECTION

PATENT NO. : 5,422,376
DATED : 06/06/95
INVENTOR(S) : Bradford C. Webb

It is certified that error appears in the above-indentified patent and that said Letters Patent is hereby corrected as shown below:

Col. 6 lines 67-68 should be changed to read

"The following example embodies features of the present invention"

Signed and Sealed this

Tenth Day of October, 1995

*Attest:*

BRUCE LEHMAN

*Attesting Officer*  *Commissioner of Patents and Trademarks*